US006328981B1

(12) United States Patent
Boussouira et al.

(10) Patent No.: US 6,328,981 B1
(45) Date of Patent: *Dec. 11, 2001

(54) COMPOSITION COMPRISING A DIBENZOYLMETHANE DERIVATIVE AND A POLYAMINO POLYMER

(75) Inventors: Boudiaf Boussouira, Paris; Didier Candau, Bievres, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,032

(22) Filed: May 22, 1998

(30) Foreign Application Priority Data

May 28, 1997 (FR) .................................................. 97 06531

(51) Int. Cl.⁷ ................................ A61K 7/42; A61K 7/00
(52) U.S. Cl. ............................ 424/401; 424/59; 424/60; 424/70.11; 424/70.17; 514/938; 514/242; 514/679
(58) Field of Search ............................. 424/401, 59, 60, 424/70.11, 70.17; 514/938, 242, 679

(56) References Cited

U.S. PATENT DOCUMENTS

| 4,144,123 | 3/1979 | Scharf et al. .................... 162/164 |
| 4,360,646 | 11/1982 | Denkewalter et al. .............. 525/420 |
| 4,631,337 | 12/1986 | Tomalia et al. ................... 528/391 |
| 4,694,064 | 9/1987 | Tomalia et al. ................... 528/332 |
| 4,871,530 | * 10/1989 | Grollier et al. .................... 424/47 |
| 5,204,099 | 4/1993 | Barbier et al. .................... 424/401 |
| 5,449,519 | 9/1995 | Wolf et al. ....................... 424/401 |
| 5,556,616 | 9/1996 | Janchitraponvej et al. .... 424/70.122 |
| 5,616,331 | * 4/1997 | Allard et al. ..................... 424/401 |
| 5,733,895 | * 3/1998 | Forestier et al. .................. 514/63 |
| 5,882,663 | * 3/1999 | Pisson et al. ..................... 424/59 |
| 5,904,735 | * 5/1999 | Gutierrez et al. .................. 8/137 |
| 5,910,513 | * 6/1999 | Galey ............................ 514/649 |

FOREIGN PATENT DOCUMENTS

| 3 743 744 | 7/1989 | (DE) . |
| 0 114 607 | 8/1984 | (EP) . |
| 0 487 404 | 5/1992 | (EP) . |
| 0 518 772 | 12/1992 | (EP) . |
| 0 518 773 | 12/1992 | (EP) . |
| 0 541 018 | 5/1993 | (EP) . |
| 0 590 538 | 4/1994 | (EP) . |
| 0 682 059 | 11/1995 | (EP) . |
| 0 684 044 | 11/1995 | (EP) . |
| 0 782 846 | 7/1997 | (EP) . |
| 0 816 324 | 1/1998 | (EP) . |
| 1 477 147 | 4/1967 | (FR) . |
| 2 315 991 | 1/1977 | (FR) . |
| 2 326 405 | 4/1977 | (FR) . |
| 2 416 008 | 8/1979 | (FR) . |
| 2 440 933 | 6/1980 | (FR) . |
| 2 658 076 | 8/1991 | (FR) . |
| 69007395 | 9/1968 | (JP) . |
| 3-183620 | 8/1991 | (JP) . |
| WO 90/09777 | 9/1990 | (WO) . |
| WO 93/04665 | 3/1993 | (WO) . |
| WO 93/04666 | 3/1993 | (WO) . |
| WO 93/14147 | 7/1993 | (WO) . |
| WO 94/12560 | 6/1994 | (WO) . |
| WO 94/14873 | 7/1994 | (WO) . |
| WO 94/20681 | 9/1994 | (WO) . |
| WO 94/29422 | 12/1994 | (WO) . |
| WO 95/02008 | 1/1995 | (WO) . |
| WO 96/12754 | 5/1996 | (WO) . |
| WO 96/14345 | 5/1996 | (WO) . |
| WO 96/14346 | 5/1996 | (WO) . |
| WO 96/29080 | 9/1996 | (WO) . |
| WO 97/14404 | 4/1997 | (WO) . |

OTHER PUBLICATIONS

Nicole Ardoin et al., "Molecular trees: from syntheses towards applications", Bull. Soc. Cim. Fr. (1995) 132, 875–909.

A.D. Bangham et al., "Diffusion of Univalent Ions across the lamellae of Swollen Phospholipids", J. Mol. Biol. (1965) 13, 238–252.

D.H. Davies et al., "Copolymerization of Acrylic Acid with 1–Substituted Imidazoles", Macromolecules, vol. 6, No. 2, Mar.–Apr. 1973, pp. 163–168.

Craig J. Hawker et al., Preparation of Polymers with Controlled Molecular Architecture. A New Convergent Approach to Dendritic Macromolecules, J. Am. Chem. Soc. 1990, 112, 7638–7647.

Kirk–Othmer, Encyclopedia of Chemical Technology, Third Edition, vol. 20, pp. 214–216.

Harold N. Feigenbaum, "Polyethylenimine: Prospective Applications", Cosmetics & Toiletries, vol. 108, Aug. 1993, pp. 73–77.

C.G. Overberger et al., "Esterolytic Activities of Copolymers Containing Imidazole Groups", Annals of the New York Academy of Sciences, vol. 155, Art. 2, Jan. 27, 1969, pp. 431–446.

C.G. Overberger et al., "Imidazole–containing Polymers. Synthesis and Polymerization of the Monomer 4(5)–Vinylimidazole", Journal of the American Chemical Society, vol. 85, No. 7, Apr. 5, 1963, pp. 951–955.

"Synthesis and Polymerization of 2–Vinylimidazole and 2–Vinylbenzimidazole", Polymer Letters Edition, John Wiley & Sons, Inc., vol. 11, (1973), pp. 465–469.

(List continued on next page.)

Primary Examiner—Thurman K. Page
Assistant Examiner—Lakshmi Channavajjala
(74) Attorney, Agent, or Firm—Finnegan, Henderson, Farabow, Garrett & Dunner, L.L.P.

(57) ABSTRACT

Cosmetic and/or dermatalogoical compositions comprising, in a cosmetically and/or dermatologically acceptable vehicle, i) a dibenzoylmethane derivative, in particular 4-tert-butyl-4'-methoxydibenzoylmethane, and ii) at least one polyamino polymer. These compositions are particularly photostable.

39 Claims, No Drawings

OTHER PUBLICATIONS

Mitchell L. Schlossman, "Treated Pigments, New Ways to Impart Color on the Skin", Cosmetics & Toiletries, vol. 105, Feb. 1990, pp. 53–64.

James P. Tam, "Synthetic peptide vaccine design: Synthesis and properties of a high–density multiple antigenic peptide system", Proc. Natl. Acad. Sci, vol. 85, Aug. 1988, pp. 5409–5413.

Jiro Tanaka, "Copolymerization Behavior of N–Vinylimidazole with Various Dialkyl maleates and Fumarates", J. Macromol. Sci.–Chem, A21(2), (1984), pp. 253–265.

Donald A. Tomalia, "Starburst Dendrimers: MolecularLevel Control Size, Shape, Surface Chemistry, Topology, and Flexibility from Atoms to Macroscopic Matter", Angewandte Chemie, vol. 29, No. 2, Feb. 1990, pp. 138–175.

B.I. Voit, "Dendritic polymers: from aesthetic macromolecules to commercially interesting materials", Acta Polymer., 46, (1995), pp. 87–99.

* cited by examiner

COMPOSITION COMPRISING A DIBENZOYLMETHANE DERIVATIVE AND A POLYAMINO POLYMER

Applicants reference herein the patent applications of BOUDIAF BOUSSOUIRA and DIDIER CANDAU for COMPOSITION COMPRISING A CINNAMIC ACID DERIVATIVE AND A POLYAMINO POLYMER (Docket No. 05725.0305) and of BOUDIAF BOUSSOUIRA and CHRISTIAN COLIN for COSMETIC USE OF SELECTED POLYAMINO POLYMERS AS ANTIOXIDANTS (Docket No. 05257.0306), filed on even date herewith and incorporate the disclosures thereof specifically by reference herein.

The present invention relates to novel cosmetic and/or dermatological compositions (hereinafter known as anti-sun compositions) intended for protecting the skin and/or hair against UV radiation, in particular solar radiation. More specifically, it relates to novel cosmetic and/or dermatological compositions exerting an improved photostability and comprising, in a cosmetically and/or dermatologically acceptable vehicle, the combination of at least one UV screening agent derived from dibenzoylmethane and at least one polyamino polymer.

The invention also relates to the use of these compositions in the cosmetic and/or dermatological fields.

It is known that light radiation with wavelengths ranging from 280 nm to 400 nm makes it possible for the human skin to brown and that radiation with wavelengths more particularly from 280 to 320 nm, known under the name of UV-B, causes erythemas and skin burns which can harm the development of natural tanning. For these reasons and for aesthetic reasons, there exists a continual demand for means for controlling this natural tanning, for the purpose of thus controlling the colour of the skin; it is thus advisable to screen out this UV-B radiation.

It is also known that UV-A radiation, with wavelengths ranging from 320 to 400 nm, which causes the skin to brown, is capable of leading to a detrimental change in the latter, especially in the case of sensitive skin or skin which is continually exposed to solar radiation. In particular, UV-A radiation causes a loss of skin elasticity and the appearance of wrinkles, leading to premature skin ageing. It promotes the triggering of the erythemal reaction or accentuates this reaction in certain subjects and can even be the cause of phototoxic or photoallergic reactions. Thus, for aesthetic and cosmetic reasons, such as preservation of the natural elasticity of the skin, for example, more and more people wish to control the effect of UV-A radiation on their skin. It is thus desirable to screen out the UV-A radiation as well.

Thus, with the aim of providing protection of the skin and hair against all UV radiation which is as complete and as efficient as possible, use is generally made, in the manufacture of anti-sun compositions, of combinations of screening agents active in the UV-A and of screening agents active in the UV-B.

In this respect, a particularly advantageous family of UV-A screening agents is currently composed of dibenzoylmethane derivatives, in particular 4-tert-butyl-4'-methoxydibenzoylmethane, because these exhibit a strong intrinsic absorption power. These dibenzoylmethane derivatives, which are now products well known per se as screening agents active in the UV-A, are described in particular in French Patent Applications FR-A-2,326,405 and FR-A-2,440,933, and in European Patent Appliiation EP-A-0,114,607, the disclosures of which are specifically incorporated by reference herein.

However, the inventors have found that these dibenzoylmethane derivatives, in particular 4-tert-buty-4'-methoxydibenzoylmethane, when they are exposed to UV irradiation, exhibit the disadvantage of chemically degrading to a significant extent. In particular, the inventors found that these dibenzoylmethane derivatives underwent peroxidation reactions when they were exposed to UV radiation.

In addition to the problem of the photodegradation of the dibenzoylmethane derivatives themselves, the inventors have found that the dibenzoylmethane, when it is combined with certain other organic screening agents, exhibits the disadvantage of causing the photodegradation of these screening agents when this combination is exposed to UV radiation.

1,3,5-Triazine derivatives, in particular 2,4,6-tris[p-(2'-ethylhexyl-1'-oxycarbonyl)anilino]-1,3,5-triazine, sold under the tradename "UVINUL T 150" by the company BASF, possess a strong absorbing power for UV-B radiation. It would therefore be very advantageous to be able to use them in combination with the 4-tert-butyl-4'-methoxydibenzoylmethane mentioned above with the aim of obtaining products offering broad and effective protection in the whole range of UV radiation.

However, the inventors have found that these 1,3,5-triazine derivatives, when they are brought together with dibenzoylmethane derivatives, in particular 4-tert-butyl-4'-methoxydibenzoylmethane, and placed under UV irradiation, exhibit the disadvantage of chemically degrading to a significant extent. Under these conditions, the combination of the two screening agents no longer allows prolonged broad anti-sun protection of the skin and hair.

Now, following significant research carried out in the field of the photoprotection mentioned above, the inventors have now discovered that:

the combination of certain polyamino polymers, which will be defined hereinbelow, with a dibenzoylmethane derivative, in particular 4-tert-butyl-4'-methoxydibenzoylmethane, made it possible in an entirely remarkable way to improve the photostability of this dibenzoylmethane derivative when it is exposed to UV radiation and thus to improve the overall efficiency of these screening agents;

the combination of certain polyamino polymers, which will be defined hereinbelow, with a dibenzoylmethane derivative and another organic screening agent selected from 1,3,5-triazine derivatives made it possible in an entirely remarkable way to improve the photostability of the 1,3,5-triazine derivatives in the presence of this dibenzoylmethaine derivative when the combination is exposed to UV radiation and thus to improve the overall efficiency of the dibenzoylmethane derivative+ 1,3,5-triazine derivative screening combination.

A subject-matter of the present invention is thus novel cosmetic anchor dermatological compositions comprising, in a cosmetically and/or dermatologicially acceptable vehicle:

a) at least one polyamino polymer as defined hereinbelow;

b) at least one dibenzoylmethane derivative corresponding to the following formula (V):

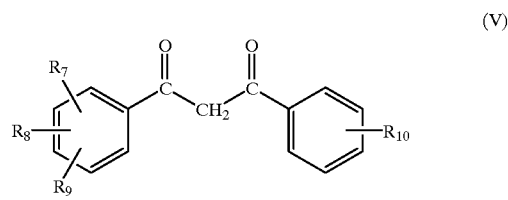

(V)

in which $R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical.

Thus, according to the present invention, cosmetic and/or dermatological compositions can be prepared containing a dibenzoylmethane derivative, in particular 4-tert-butyl-4'-methoxydibenzoylmethane, in which compositions the concentration of dibenzoylmethane derivative remains relatively constant even if these compositions are subjected to the action of light.

Another subject-matter of the invention is a cosmetic and/or dermatological composition comprising, in a cosmetically and/or dermatologically acceptable vehicle:

a) at least one polyamino polymer;

b) at least one dibenzoylmethane derivative corresponding to the following formula (V):

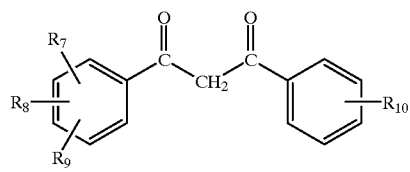

(V)

in which $R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical;

c) at least one 1,3,5-triazine derivative corresponding to the following formula (I):

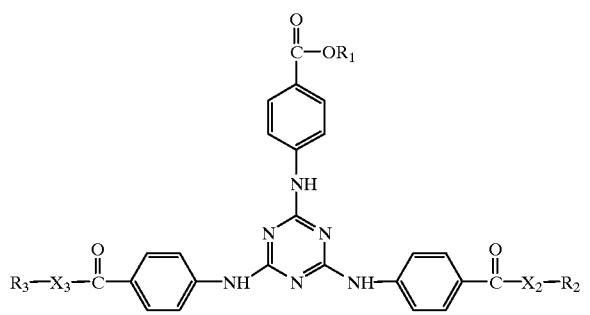

(I)

in which:

$X_2$ and $X_3$ independently represent oxygen or the —NH— radical;

$R_1$, $R_2$ and $R_3$ independently are selected from: hydrogen; alkali metals; ammonium radicals optionally substituted by one or more alkyl or hydroxyalkyl radicals; linear and branched $C_1$–$C_{18}$ alkyl radicals; $C_5$–$C_{12}$ cycloalkyl radicals optionally substituted by one or more $C_1$–$C_4$ alkyl radicals; polyoxyethylene radicals comprising from 1 to 6 ethylene oxide units, in which the terminal OH group is methylated; radicals of following formula (II), (III) and (IV):

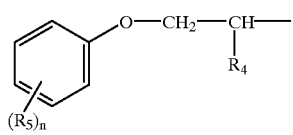

(II)

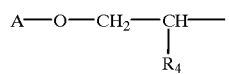

(III)

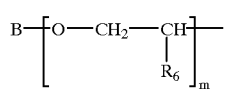

(IV)

in which:

$R_4$ is hydrogen or a methyl radical;

$R_5$ is a $C_1$–$C_9$ alkyl radical;

n is an integer ranging from 0 to 3;

m is an integer ranging from 0 to 10;

A is a $C_4$–$C_8$ alkyl radical or a $C_5$–$C_8$ cycloalkyl radical;

B is selected from: linear and branched $C_1$–$C_8$ alkyl radicals; $C_5$–$C_8$ cycloalkyl radicals; aryl radicals optionally substituted by one or more $C_1$–$C_4$ alkyl radicals;

$R_6$ is hydrogen or a methyl radical.

Of course, in the above definition, when $X_2$ and/or $X_3$ represent a —NH— radical, then the corresponding $R_2$ and/or $R_3$ radical or radicals are other than an alkali metal or an ammonium radical.

Thus, according to the present invention, cosmetic and/or dermatological compositions can be prepared containing a dibenzoylmethane derivative, in particular 4-tert-butyl-4'-methoxydibenzoylmethane, in combination with at least one 1,3,5-triazine derivative, in which compositions the concentration of 1,3,5-triazine derivative remains relatively constant even if these compositions are subjected to the action of light.

A further subject-matter of the present invention is the use of a polyamino polymer in, or for the manufacture of, cosmetic and/or dermatological compositions containing a dibenzoylmethane derivative as defined above for the purpose of improving, in the compositions, the stability to UV radiation (photostability) of the dibenzoylmethane derivative.

Another subject-matter of the present invention is a process for improving the stability to UV radiation (photostability), and thus the efficiency, of a cosmetic and/or dermatological composition comprising a dibenzoylmethane derivative as defined above, the process involving introducing an effective amount of a polyamino polymer into the composition.

A further subject-matter of the present invention is the use of a polyamino polymer as defined hereinbelow in, or for the manufacture of, cosmetic and/or dermatological compositions containing a dibenzoylmethane derivative, in combination with at least one 1,3,5-triazine derivative as defined above, for the purpose of improving, in the compositions, the stability to UV radiation (photostability) of the 1,3,5-triazine derivative.

Another subject-matter of the present invention is a process for improving the stability to UV radiation (photostability), and thus the efficiency, of a cosmetic and/or dermatological composition comprising a dibenzoylmethane derivative and a 1,3,5-triazine derivative as defined above, the process involving introducing an effective amount of a polyamino polymer as defined hereinbelow into the composition.

"Effective amount of polyamino polymer" is understood to mean an amount sufficient to produce a noteworthy and significant improvement in the photostability of the dibenzoylmethane derivative or derivatives contained in the composition. This minimum amount of stabilizing agent to be employed, which can vary according to the nature of the cosmetically acceptable vehicle used in the composition, can be determined without any difficulty by means of a conventional test for the measurement of photostability, such as that given in the examples hereinafter.

Other characteristics, aspects and advantages of the present invention will become apparent on reading the detailed description which will follow.

The polyamino polymers of the invention are selected from the following families:

(A) a polyalkylene polyamine or a polyalkylene polyamine derivative selected from:
  (i) polyalkylene polyamines;
  (ii) alkylated derivatives of polyalkylene polyamines (A)(i);
  (iii) addition products of alkylcarboxylic acids with polyalkylene polyamines (A)(i);
  (iv) addition products of ketones and aldehydes with polyalkylene polyamines (A)(i);
  (v) addition products of isocyanates and isothiocyanates with polyalkylene polyamines (A)(i);
  (vi) addition products of alkylene oxide and poly(alkylene oxide) block polymers with polyalkylene polyamines (A)(i);
  (vii) quaternized derivatives of polyalkylene polyamines (A)(i);
  (viii) addition products of a silicone with polyalkylene polyamines (A)(i);
  (ix) a copolymer of dicarboxylic acid and polyalkylene polyamines (A)(i);
(B) polyvinylimidazoles;
(C) polyvinylpyridines;
(D) addition products of 1-vinylimidazole monomers of formula (1):

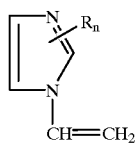

(I)

in which the R radicals independently represent H or a saturated or unsaturated, linear or cyclic, $C_1$–$C_6$ alkyl radical, n is an integer ranging from 1 to 3, with polyalkylene polyamines (A)(i) to (A)(ix);
(E) polymers based on amino acids containing a basic side chain;
(F) crosslinked derivatives of the polymers (A)(i) to (A)(ix), (B), (C), (D) and (E).

The polyamino polymers which can be used in the present invention can be in the linear polymer, hyperbranched polymer or dendrimer form.

Hyperbranched polymers are molecular constructions having a branched structure, generally around a core. Their structure is generally devoid of symmetry: the base units or monomers which have been used in the construction of the hyperbranched polymer can be different in nature and their distribution is irregular. The branches of the polymer can be different in nature and in length. The number of base units, or monomers, can be different depending on the different branching. While being asymmetric, hyperbranched polymers can have: an extremely branched structure, around a core; successive layers or generations of branching; a layer of terminal chains.

Hyperbranched polymers generally result from the polycondensation of one or more monomers ABx, A and B being reactive groups capable of reacting together and x being an integer greater than or equal to 2, but other preparation processes can be envisaged. Hyperbranched polymers are characterized by their degree of polymerization DP=1-b, b being the percentage of non-terminal functionalities in B which have not reacted with a group A. As the condensation is non-systematic, in contrast to the synthesis of dendrimers, the degree of polymerization is less than 100%. Usually, by known synthetic methods, DP ranges from 15 to 90%. A terminal group T on the hyperbranched polymer can be made to react in order to obtain a specific functionality at the chain end.

Such polymers are described in particular in B.l. Voit, Acta Polymer., 46, 87–99 (1995); EP-682,059; WO-9614346; WO-9614345; WO-9612754, the disclosures of which are specifically incorporated by reference herein.

Several hyperbranched polymers can be combined with one another, via a covalent bond or another type of bond, by means of their terminal groups. Such so-called bridged polymers come within the definition of hyperbranched polymers according to the present invention.

Dendrimers are highly branched polymers and oligomers, which are also known, having a well defined chemical structure and they are said to be "perfect" hyperbranched polymers. As a general rule, dendrimers comprise a core, a defined number of generations of branches, or spindles, and terminal groups. The generations of spindles are composed of structural units which are identical for the same generation of spindles and which can be identical or different for different generations of spindles. The generations of spindles extend radially in a geometrical progression from the core. The terminal groups of a dendrimer of the Nth generation are the terminal functional groups of the spindles of the Nth generation or terminal generation. Such polymers are described in particular in D. A. Tomalia, A. M. Naylor and W. A. Goddard III, *Angewandte Chemie*, Int. Ed. Engl., 29, 138–175 (1990); C. J. Hawker and J. M. J. Frechet, *J. Am. Chem. Soc.*, 112, 7638 (1990); B. 1. Voit, Acta Polymer., 46, 87–99 (1995); N. Ardoin and D. Astruc, Bull. Soc. Chim. Fr., 132, 875–909 (1995), the disclosures of which are specifically incorporated by reference herein.

Dendrimers can also be defined more particularly by the following formula (Dl):

in which:
  C represents the core, connected via a number s of functionalities to s spindles $A_1B_1$ via groups $A_1$;
  s is an integer greater than or equal to 1 and less than or equal to the number of functionalities in C;
  the index i (i=1, 2 . . . n) is an integer which denotes the generation of each spindle;
  $r_i$(i=1, 2 . . . n−1) represents the number of functionalities in the group $B_i$ belonging to the spindle ($A_iB_i$), $r_i$ being an integer greater than or equal to 2;
  for each spindle ($A_iB_i$) (i=1, 2 . . . n), the group $B_i$ is connected to $r_i$ groups $A_{i+1}$ of a spindle ($A_{i+1}B_{i+1}$);
  each group $A_i$ (i≧2) is connected to only one group $B_{i-1}$ of the spindle ($A_{i-1}B_{i-1}$);
  the spindle of nth generation $A_nB_n$ is chemically bonded to a number $r_n$ of terminal groups T, $r_n$ being an integer greater than or equal to zero.

The definition of dendrimers given above includes molecules with symmetrical branching; it also includes molecules with non-symmetrical branching, such as, for example, dendrimers in which the spindles are lysine groups, in which the branching of one generation of spindles on the preceding generation takes place on the α and ε amines of the lysine, which results in a difference in the length of the spindles for the different branching.

Dense star polymers, starburst polymers and rod-shaped dendrimers are included in the present definition of dendrimers. The molecules known as arborols and cascade molecules also come within the definition of dendrimers according to the present invention.

Several dendrimers can be combined with one another via a covalent bond or another type of bond, by means of their terminal groups, to give entities known under the name of "bridged dendrimers". Such entities are included in the definition of dendrimers according to the present invention.

Dendrimers can exist in the form of an assembly of molecules of the same generation, which are so-called monodisperse assemblies; they can also exist in the form of assemblies of different generations, which are so-called polydisperse assemblies. The definition of dendrimers according to the present invention includes both monodisperse and polydisperse assemblies of dendrimers.

Reference may be made to the following documents, in which are described dendrimers containing amine functional groups, the contents of these documents being incorporated by reference in the present description: U.S. Pat. No. 4,694,064; U.S. Pat. No. 4,631,337; WO-A-9502008; WO-A-9314147; U.S. Pat. No. 4,360,646; Proc. Natl. Acad. Sci. USA, 85, 5409–5413 (1988), the disclosures of which are specifically incorporated by reference herein.

Hyperbranched polymers and dendrimers containing amino functional groups can also be composed of a core and of generations of base units, monomers or spindles, of any nature, on which a terminal group T carrying an amine functional group has been grafted.

The polyamino polymers (A)(i) to (A)(ix), (B), (C), (D), (E) and (F) of the invention will be described in greater detail: (A)(i) the polyalkylene polyamines preferably used according to the invention are polymers containing from 7 to 20,000 repeat units. The choice is preferably made of polyalkylene polyamines comprising at least 5% of tertiary amines, advantageously at least 10% of tertiary amine functional groups and more preferably still at least 20%. These polymers can be homopolymers or copolymers which are linear, branched or of dendrimer structure.

These polymers comprise the following repeat units:

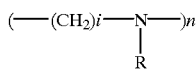

in which:
i represents an integer greater than or equal to 2, preferably i=2;
n represents an integer
R represents H or a unit

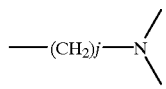

in which j represents an integer greater than or equal to 2, preferably j=2.

Among the products of the family of polyalkylene polyamines, also known as polyaziridines, mention may in particular be made of: polyethyleneimine, which is a hyperbranched polymer well known to a person skilled in the art: on the subject of polyethyleneimine, reference may be made in particular to the documents: "Kirk-Othmer Encyclopedia of Chemical Technology", 3rd edition, Vol. 20, 1982, p. 214–216 and "Polyethyleneimine Prospective Application", H. N. Feigenbaum, Cosmetic & Toiletries, 108, 1993, p. 73, the disclosures of which are specifically incorporated by reference herein. Polyethyleneimine is available commercially from the company BASF under the tradenames LUPASOL and POLYIMIN; polyethyleneimine is usually within an average molecular weight range from 500 to 2,000,000.

Polyethyleneimines and polypropyleneimines in the form of dendrimers, manufactured by the company DSM, are also known. Patent Applications WO 95/02008 and WO 93/14147, the disclosures of which are specifically incorporated by reference herein, describe polyalkylene polyamines from the family of the dendrimers and a process for their preparation. (A)(ii) alkylated derivatives of polyalkylene polyamines are products well known to a person skilled in the art. They are obtained in a known way by alkylation, in aqueous or alcoholic medium, in the presence of an alkylating agent, preferably in the presence of NaOH, of KOH or of carbonate, at temperatures preferably ranging from 40° C. to 130° C. The alkylating agent can be selected, for example, from $C_1$–$C_8$ alkyl halide or alkyl sulphate derivatives, such as, for example, dimethyl sulphate, diethyl sulphate, butyl bromide, hexyl bromide, 2-ethylhexyl bromide, noctyl bromide or the corresponding chlorides. Reference may be made, for example, to DE-3743744, which describes the preparation of such products, the disclosure of which is specifically incorporated by reference herein. (A)(iii) addition products of alkylcarboxylic acids with polyalkylene polyamines are products known to a person skilled in the art, the preparation of which is described, for example, in Patent Applications WO 94/14873, WO 94/20681 and WO 94/12560, the disclosures of which are specifically incorporated by reference herein. The addition of alkylcarboxylic acids to polyalkylene polyamines can be carried out by reacting, in a known way, an acid, an amide, an ester or an acid halide with the polyalkylene polyamine polymer.

Addition products of alkylcarboxylic acids with polyalkylene polyamines can be, for example, the addition products of saturated or unsaturated, linear or branched, $C_2$–$C_{30}$ alkylcarboxylic acids with a polyethyleneimine. Mention may be made, among the carboxylic acids which can be used, of, for example, acetic acid, propionic acid, butyric acid, 2-ethylhexanoic acid, benzoic acid, lauric acid, myristic acid, palmitic acid, stearic acid, oleic acid, linoleic acid, arachidonic acid or behenic acid, and mixtures of fatty substances, such as, for example, mixtures of fatty esters available in the form of natural products and among which may be mentioned: coconut oil, soybean oil, linseed oil or rapeseed oil. (A)(iv) addition products of ketones and aldehydes with polyalkylene polyamines (A)(i) can be prepared by processes known to a person skilled in the art and result in α-hydroxy-amine units being obtained; (A)(v) addition products of isocyanates and isothiocyanates with polyalkylene polyamines (A)(i) can be prepared by processes known to a person skilled in the art and result in urea and thiourea units being obtained; (A)(vi) addition products of alkylene oxide and poly(alkylene oxide) block polymers with polyalkylene polyamines (A)(i) can be prepared by processes known to a person skilled in the art; reference may be made, for example, to the documents EP-541,018 and U.S. Pat. No. 4,144,123, the disclosures of which are specifically incorporated by reference herein, in which such molecules are described; ethoxylated polyethyleneimine derivatives are available commercially under the tradename: LUPASOL 61 (BASF); (A)(vii) quaternized derivatives of polyalkylene polyamines (A)(i) can be prepared by processes known to a person skilled in the art;

(A)(viii) addition products of a silicone with polyalkylene polyamines (A)(i) are, for example, polyethyleneimines grafted by polydimethylsiloxane units, the preparation of which is described in the document U.S. Pat. No. 5,556,616 (the disclosure of which is specifically incorporated by reference herein), which are sold by the company MacIntyre under the tradename MACKAMER PAVS; (A)(ix) copolymers of dicarboxylic acid and of polyalkylene polyamines (A)(i) can be prepared by polycondensation of dicarboxylic acids with polyalkylene polyamines.

Mention may be made, among dicarboxylic acids which can be used for the preparation of the polyamidoamines, of $C_2$ to $C_{10}$ dicarboxylic acids, such as, for example, oxalic acid, malonic acid, itaconic acid, succinic acid, maleic acid, adipic acid, glutaric acid, sebacic acid, terephthalic acid or orthophthalic acid, and their mixtures.

The polyalkylene polyamines used for the preparation of the polyamidoamines are advantageously selected from those having from 3 to 10 nitrogen atoms, such as, for example, diethylenetriamine, triethylenetetramine, dipropylenetriamine, tripropylenetetramine, dihexamethylenetriamine, aminopropylethylenediamine, bisaminopropylethylenediamine and their mixtures. Use may also be made of polyethyleneimines, such as described above, for the preparation of polyamidoamines.

Such compounds are described, for example, in the documents: U.S. Pat. No. 4,144,423 and WO 94/29422, the disclosures of which are specifically incorporated by reference herein. (B) the term polyvinylimidazole comprises the homopolymers and copolymer; of polyvinylimidazole (PVI) obtained by radical polymerization of the vinylimidazole monomers with the following structure:

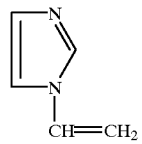

The copolymers can be, for example, copolymers of vinylimidazole containing at least 5% of vinylimidazole units with monomers selected from the units: vinylpyrrolidinone, acrylic acid and acrylamide. The synthesis of such compounds is well known to a person skilled in the art; in this respect, reference may in particular be made to the documents: J. Am. Chem. Soc., Vol. 85, 1962, p. 951; Polymer Letters Ed., Vol. 11, 1973, p. 465–469; Macromolecules, Vol. 6(2), 1973, p. 163–168; Ann. N.Y. Acad. Sci., Vol. 155, 1969, p. 431; FR-A-1,477,147; JP-69 07395; J. Macromol. Scien. Chem., Vol. A21(2), 1984, p. 253, the disclosures of which are specifically incorporated by reference herein. (C) the term polyvinylpyridine comprises the homopolymers and copolymers of vinylpyridine obtained by radical polymerization of the vinylpyridine monomers (substituted at the 2- or 4-position of the pyridine nucleus) with the following structure:

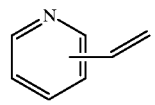

The copolymers can be, for example, copolymers of vinylpyridine containing at least 5% of vinylpyridine units with monomers selected from the units: vinylpyrrolidinone, acrylic acid and acrylamide. (D) addition products of 1-vinylimidazole monomers corresponding to the formula (I):

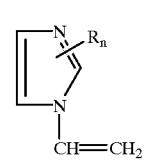

in which the R radicals independently represent H or a saturated or unsaturated, linear or cyclic, $C_1$–$C_6$ alkyl radical, n is an integer ranging from 1 to 3 with polyalkylene polyamines and their derivatives (A)(i) to (A)(ix).

Mention may be made, among the derivatives of formula (I) which can be used, of, for example, 2-methyl-1-vinylimidazole or 2-benzyl-1-vinylimidazole. These products are known to a person skilled in the art. Their preparation is described, for example, in Patent Application WO 94129422, the disclosure of which is specifically incorporated by reference. (E) polymers based on amino acids containing a basic side chain are preferably selected from proteins and peptides containing at least 5%, advantageously at least 10%, of amino acids selected from histidine, lysine or arginine.

Mention may be made, among these polymers, of, for example, polylysines or polyhistidines. (F) crosslinked derivatives of the polymers (A)(i) to (A)(ix), (B), (C) and (D). Mention may be made, among the crosslinking agents which can be used, of halohydrin-, glycidyl, aziridino- or isocyanate derivatives; such crosslinking agents and their methods of use are well known to a person skilled in the art. Mention may be made, among the most well known, of: epichlorohydrin, α,ω-bis(chlorohydrin)polyalkylene glycol ethers, or α,ω-dichloroalkanes, such as, for example, 1,2-dichloroethane, 1,2-dichloropropane, 1,3-dichloropropane, 1,4-dichlorobutane and 1,6-dichlorohexane; such crosslinking agents and their use in crosslinking polyethyleneimine derivatives are described in WO 94/12560, the disclosure of which is specifically incorporated by reference herein.

Preferably, polyamino polymers comprising at least 5% of tertiary amines, advantageously at least 10% of tertiary amine functional groups and more preferentially still at least 20% are selected in the implementation of the present invention.

According to the invention, the polyamino polymer is advantageously selected from:
(A)
  (i) hyperbranched polyethyleneimines,
  (ii) alkylated polyethyleneimine derivatives;
  (iii) addition products of alkylcarboxylic acids with polyethyleneimine;
  (iv) addition products of ketones and aldehydes with polyethyleneimine;
  (v) addition products of isocyanates and isothiocyanates with polyethyleneinine;
  (vi) addition products of alkylene oxide andf poly (alkylene oxide) block polymers with polyethyleneimine;
  (vii) quaternized derivatives of polyethyleneimine;
  (viii) addition products of a silicone with polyethyleneimine;
  (ix) copolymers of dicarboxylic acid and of polyethyleneimine;
(B) polyvinylimidazoles.

More preferably still, the polyamino polymer is selected from: (A) (i) hyperbranched polyethyleneimines. Preferably, polyethyleneimines comprising at least 5% of tertiary amines, advantageously at least 10% of tertiary amine functional groups and more preferably still at least 20% are selected.

The polyamino polymer is advantageously introduced into the compositions according to the invention in a neutralized form.

Generally, the polyamino polymer or polymers can be present in the compositions in accordance with the invention at contents generally ranging from 0.01% to 50% by weight and more preferably from 0.1% to 30% by weight, with respect to the total weight of the composition.

A person skilled in the art will know how to adjust, by simple tests, the proportions of polyamino polymer with respect to the dibenzoylmethane derivative and optionally with respect to the other components of the composition, in particular the 1,3,5-tiazine. This is because the optimum proportions of the various constituents can vary, for example as a function of the molecular weight of the polymer, of the level of amines and/or of the level of tertiary amines in this polymer.

As indicated above, the dibenzoylmethane derivatives which can be used according to the present invention are those corresponding to the following formula (V):

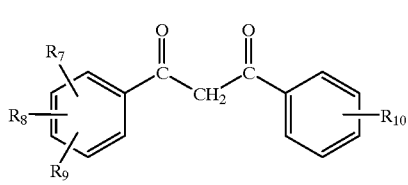

(V)

in which:

$R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical.

According to the present invention, it is possible, of course, to employ one or more dibenzoylmethane derivatives.

Mention may in particular be made, among the dibenzoylmethane derivatives which can be used according to the present invention, of, without implied limitation:

2-methyidibenzoylmethane,
4-methyldibenzoylmethane,
4-isopropyldibenzoylmethane,
4-tert-butyidibenzoylmethane,
2,4-dimethyidibenzoylmethane,
2,5-dimethyldibenzoylmethane,
4,4'-diisopropyidibenzoylmethane,
4-tert-butyl-4'-methoxydibenzoylmethane,
2-methyl-5-isopropyl-4'-methoxydibenzoylmethane,
2-methyl-5tert-butyl-4'-methoxydibenzoylmethane,
2,4-dimethyl-4'-methoxydibenzoylmethane,
2,6-dimethyl-4-tert-butyl-4'-methoxydibenzoylmethane,
4,4'dimethoxydibenzoylmethane.

These products are already well known and are described in particular in the above mentioned documents FR-A-2,326,405, FR-A-2,440,933 and EP-A-0,114,607, the disclosures of which are specifically incorporated by reference herein.

Among the dibenzoylmethane derivatives mentioned above, it is very particularly preferred, according to the present invention, to employ 4-tert-butyl-4'-methoxydibenzoylmethane, in particular that provided for sale under the tradename of "PARSOL 1789" by the company Givaudan, this screening agent thus corresponding to the following expanded formula:

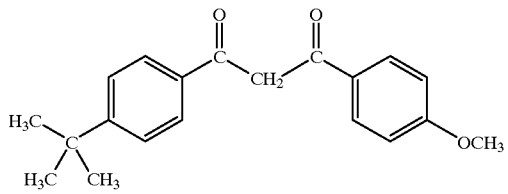

Another preferred dibenzoylmethane derivative according to the present invention is 4-isopropyldibenzoylmethane, a screening agent sold under the name of "EUSOLEX 8020" by the Company Merck and corresponding to the following expanded formula:

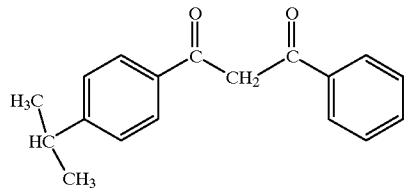

The dibenzoylmethane derivatives can be present in the compositions of the invention at a content preferably ranging from 0.2% to 15% by weight with respect to the total weight of the composition. This content more preferably ranges from 0.2% to 10%.

Thus, when a sufficient amount of a polyamino polymer is added to an anti-sun composition containing a dibenzoylmethane derivative, in particular 4-tert-butyl-4'-methoxydibenzoylmethane, an increase in the stability of the dibenzoylmethane derivative to light, and thus an improvement in the efficiency of the anti-sun composition with iime, is observed. In parallel, a decrease in the appearance of peroxidized derivatives of the dibenzoylmethane derivatives described above is observed. Another subject-matter of the invention is thus the use of a polyamino polymer as defined above as antioxidizing agent with respect to dibenzoylmethane derivatives.

The 1,3,5-triazine derivatives which can be used in the context of the present invention are selected from those corresponding to the following formula (i):

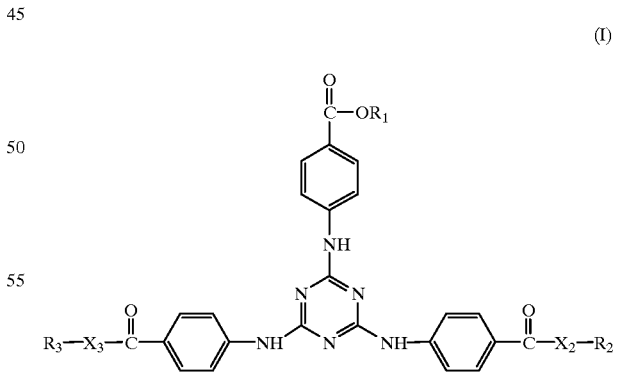

(I)

in which:

$X_2$ and $X_3$ independently represent oxygen or the —NH— radical;

$R_1$, $R_2$ and $R_3$ are independently selected from: hydrogen; alkali metals; ammonium radicals optionally substituted by one or more alkyl or hydroxyalkyl radicals; linear and branched $C_1$–$C_{18}$ alkyl radicals; $C_5$–$C_{12}$ cycloalkyl radicals optionally substituted by one or more $C_1$–$C_4$ alkyl radicals; polyoxyethylene radicals comprising from 1 to 6 ethylene oxide units, the terminal OH group of which is methylated; radicals of following formula (II), (III) and (IV):

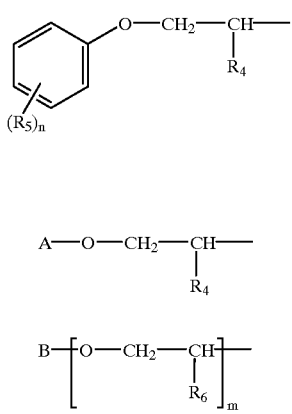

(II)

(III)

(IV)

in which:
$R_4$ is hydrogen or a methyl radical;
$R_5$ is a $C_1$–$C_9$ alkyl radical;
n is an integer ranging from 0 to 3;
m is an integer ranging from 1 to 10;
A is a $C_4$–$C_8$ alkyl radical or a $C_5$–$C_8$ cycloalkyl radical;
B is selected from: linear and branched $C_1$–$C_8$ alkyl radicals; $C_5$–$C_8$ cycloalkyl radicals; aryl radicals optionally substituted by one or more $C_1$–$C_4$ alkyl radicals;
$R_6$ is hydrogen or a methyl radical.

Of course, in the above definition, when $X_2$ and/or $X_3$ represent an —NH— radical, then the corresponding $R_2$ and/or $R_3$ radical or radicals are other than an alkali metal or an ammonium radical.

A first, more particularly preferred family of 1,3,5-triazine derivatives is that, described in particular in the document EP-A-0,517,104, the disclosure of which is specifically incorporated by reference herein, of the 1,3,5-triazines corresponding to the above formula (I) and exhibiting all the following characteristics:

$X_2$ and $X_3$ are identical and represent oxygen;
$R_1$ is selected from: $C_5$–$C_{12}$ cycloalkyl radicals optionally substituted by one or more $C_1$–$C_4$ alkyl radicals; radicals of formula (II), (III) and (IV) above in which:
B is a $C_1$–$C_4$ alkyl radical;
$R_6$ is the methyl radical;
$R_2$ and $R_3$ are independently selected from: hydrogen; alkali metals; ammonium radicals optionally substituted by one or more alkyl or hydroxyalkyl radicals; linear and branched $C_1$–$C_{18}$ alkyl radicals; $C_5$–$C_{12}$ cydoalkyl radicals optionally substituted by one or more $C_1$–$C_4$ alkyl radicals; radicals of formula (II), (III) and (IV) above in which:
B is a $C_1$–$C_4$ alkyl radical;
$R_6$ is the methyl radical.

A second preferred family of 1,3,5-triazine derivatives according to the invention is that, described in particular in the document EP-A-0,570,838, the disclosure of which is specifically incorporated by reference herein, of the 1,3,5-triazines corresponding to the formula (I) and exhibiting all the following characteristics:

$X_3$ is the —NH— radical;
$R_3$ is selected from: linear and branched $C_1$–$C_{18}$ alkyl radicals; $C_5$–$C_{12}$ cycloalkyl radicals optionally substituted by one or more $C_1$–$C_4$ alkyl radicals;
$R_1$ is selected from: hydrogen; alkali metals; ammonium radicals; radicals of formula (IV); linear and branched $C_1$–$C_{18}$ alkyl radicals; $C_5$–$C_{12}$ cycloalkyl radicals optionally substituted by one or more $C_1$–$C_4$ alkyl radicals;
if $X_2$ is the —NH— radical, then $R_2$ is selected from: linear and branched $C_1$–$C_{18}$ alkyl radicals; $C_5$–$C_{12}$ cycloalkyl radicals optionally substituted by one or more C–$C_1$ alkyl radicals;
if $X_2$ is oxygen, then $R_2$ is selected from hydrogen; alkali metals; ammonium radicals; radicals of formula (IV); linear and branched $C_1$–$C_{18}$ alkyl radicasl; $C_5$–$C_{12}$ cycloalkyl radicals optionally substituted by one or more $C_1$–$C_4$ alkyl radicals.

A particularly preferred 1,3,5-triazine of this second family is that corresponding to the following formula:

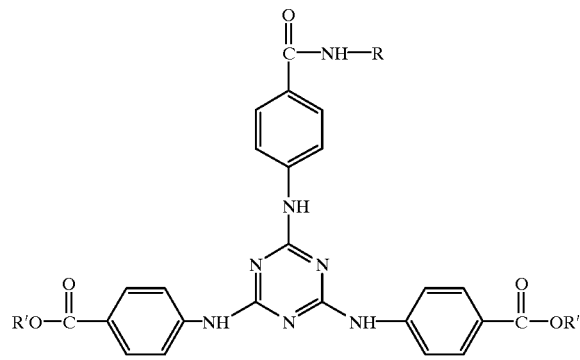

in which R' denotes a 2-ethylhexyl radical and R denotes a tert-butyl radical.

A third preferred family of compounds is that, described in particular in the document U.S. Pat. No. 4,724,137, the disclosure of which is specifically incorporated by reference herein, of the 1,3,5-triazines corresponding to the formula (I) and exhibiting all the following characteristics:

$X_2$ and $X_3$ are identical and represent oxygen;
$R_1$, $R_2$ and $R_3$ are identical and represent a $C_6$–$C_{12}$ alkyl radical or a polyoxyethylene radical comprising from 1 to 6 ethylene oxide units, the terminal OH group of which is methylated.

A particularly preferred 1,3,5-triazine of this third family is 2,4,6-tris [p(2'-ethylhexyl-1'-oxycarbonyl)anilino]-1,3,5-triazine, which is a screening agent known per se, active in the UV-B, existing in a solid form, and which is sold in particular under the trade name of "UVINUL T 150" by the Company BASF. This product corresponds to the following formula:

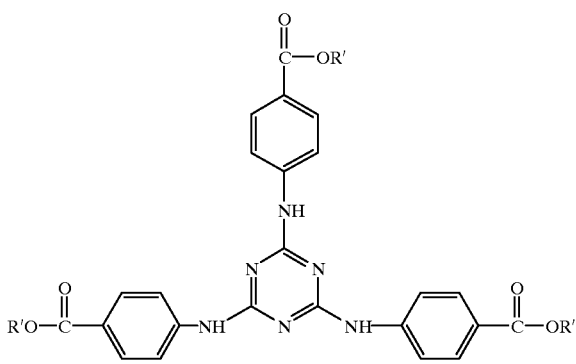

in which R' denotes a 2-ethylhexyl radical.

The 1,3,5-trazine derivative or derivatives are generally present in the compositions of the invention at a content ranging from 0.5% to 20%, more preferably from 1% to 10%, by weight with respect to the total weight of the composition.

Advantageously, the compositions according to the invention contain, in addition, at least one metal oxide nanopigment.

According to the invention, "nanopigment" is understood to mean a pigment in which the size of the primary particles preferably has a mean dimension of less than 100 nm and more preferably from 5 to 50 nm.

The metal oxides are selected from titanium, zinc, cerium or zirconium oxides or their mixtures.

The nanopigments can be coated or non-coated.

The coated pigments are pigments which have been subjected to one or more surface treatments of a chemical, electronic, mechanochemical and/or mechanical nature with compounds such as described, for example, in Cosmetics & Toiletries, February 1990, Vol. 105, p. 53–64, the disclosure of which is specifically incorporated by reference herein, such as amino acids, beeswax, fatty acids, fatty alcohols, anionic surfactants, lecithins, sodium, potassium, zinc, iron or aluminium salts of fatty acids, silicones, proteins (collagen, elastin), alkanolamines, silicon oxides, metal oxides or sodium hexametaphosphate, polyols or perfluorinated oils.

The coated pigments are more particularly titanium oxides coated:

with silica, such as the product "SUNVEIL" from the company Ikeda, with silica and iron oxide, such as the product "Sunveil F" from the company Ikeda, with silica and alumina, such as the products "MICROTITANIUM DIOXIDE MT 500 SA" and "MICROTITANIUM DIOXIDE MT 100 SA" from the company Tayca or "TIOVEIL" from the company Tioxide, with alumina, such as the products "TIPAQUE TTO-55 (B)" and "TIPAQUE TTO-55 (A)" from the company Ishihara and "UVT 14/4" from the company Kemira, with alumina and aluminium stearate, such as the product "UV TITAN M212" from the company Kemira, with alumina and aluminium stearate, such as the product "MICROTITANIUM DIOXIDE MT 100 T" from the company Tayca, with alumina and aluminium laurate, such as the product "MICROTITANIUM DIOXIDE MT 100 F" from the company Tayca, with zinc oxide and zinc stearate, such as the product "BR 351" from the company Tayca, with silica, alumina and silicone, such as the products "MICROTITANIUM DIOXIDE MT SAS" from the company Tayca, with silica, alumina and perfluoropolymethyl isopropyl ether, such as the product "TiO2 VF-25–33" from the company Toshiki, with silica, alumina, aluminium stearate and silicone, such as the product "STT-30-DS" from the company Titan Kogyo, with alumina and silicone, such as the products "TIPAQUE TTO-55 (S)" from the company Ishihara and "UV TITAN M262" from the company Kemira, with triethanolamine, such as the product "STT-65-S" from the company Titan Kogyo, with stearic acid, such as the product "TIPAQUE TTO-55 (C)" from the company Ishihara, with sodium hexametaphosphate, such as the product "MICROTITANIUM DIOXIDE MT 150 W" from the company Tayca.

It is also possible to use combinations of coated or non-coated titanium oxide nanopigments rendered dispersible in water by hydrophilic treatment or dispersible in oils by hydrophobic treatment, such as those described in European Patent Application 456,460, the disclosure of which is specifically incorporated by reference herein.

Mention may also be made of mixtures of metal oxides, in particular of titanium dioxide and of cerium dioxide, including the mixture of equal weights of silica-coated titanium dioxide and silica-coated cerium dioxide sold by the company Ikeda under the name "SUNVEIL A", and the mixture of titanium dioxide and of zinc dioxide, which are coated with alumina, silica and silicone, such as the product "M 261" sold by the company Kemira, or which are coated with alumina, silica and glycerol, such as the product "M 211" sold by the company Kemira.

The non-coated titanium oxides are, for example, sold by the company Tayca under the tradenames "MICROTITANIUM DIOXIDE MT 500 B" or "MICROTITANIUM DIOXIDE MT 600 B", by the company Degussa under the name "P 25", by the company Wacker under the name "TRANSPARENT TITANIUM OXIDE PW", by the company Miyoshi Kasei under the name "UFTR" or by the company Tomen under the name "ITS".

The non-coated zinc oxides are, for example, sold by the company Sumitomo under the name "ULTRA FINE ZINC OXIDE POWDER", by the company Presperse under the name "FINEX 25", by the company Ikeda under the name "MZO-25" or by the company Sunsmart under the name "Z-COTE".

Non-coated cerium oxide is sold under the name "COLLOIDAL CERIUM OXIDE" by the company Rhône-Poulenc.

According to the invention, coated or non-coated titanium oxide nanopigments are particularly preferred.

The concentration of metal oxide nanopigments in the cosmetic compositions according to the invention preferably ranges from 0.1 to 20% by weight with respect to the total weight of the composition and more preferably from 0.25 to 15%.

The cosmetic and/or dermatological compositions targeted by the present invention can, of course, contain one or more additional, hydrophilic or lipophilic, sunscreens active in the UV-A and/or UV-B (absorbers), other, of course, than the screening agents mentioned above. These additional screening agents can be selected in particular from cinnamic derivatives, salicylic derivatives, benzylidenecamphor derivatives, benzimidazole derivatives, triazine derivatives other than those mentioned above, benzophenone derivatives, β,β'-diphenylacrylate derivatives, p-aminobenzoic acid derivatives, or the screening polymers and screening silicones described in Application WO-93/04665, the disclosure of which is specifically incorporated by reference herein. Other examples of organic screening agents are given in European Patent Application EP-A-0,487,404, the disclosure of which is specifically incorporated by reference herein.

The compositions according to the invention can also contain agents for the artificial tanning and/or browning of the skin (self-tanning agents), such as, for example, dihydroxyacetone (DHA).

The cosmetic and/or dermatological compositions according to the invention can also contain pigments other than the nanopigments described above.

The compositions in accordance with the present invention can comprise, in addition, conventional cosmetic adjuvants selected in particular from fatty substances, organic solvents, ionic or non-ionic thickeners, softeners, antioxidants, agents for combating free radicals, opacifying agents, stabilizers, emollients, silicones, α-hydroxy acids, antifoaming agents, moisturizing agents, vitamins, fragrances, preservatives, surfactants, fillers, sequestering agents, polymers, propellants, basifying or acidifying agents, dyes or any other ingredient commonly used in the cosmetic and/or dermatological field, in particular for the manufacture of anti-sun compositions in the form of emulsions.

The fatty substances can be composed of an oil or a wax or their mixtures. Oil is understood to mean a compound which is liquid at ambient temperature. Wax is understood to mean a compound which is solid or substantially solid at ambient temperature and with a melting point generally greater than 35° C.

Mention may be made, as oils, of mineral oils (liquid petrolatum); vegetable oils (sweet almond, macadamia, blackcurrant seed or jojoba oil); synthetic oils, such as perhydrosqualene, fatty alcohols, acids or esters (such as the benzoate of $C_{12}$–$C_{15}$ alcohols sold under the tradename "FINSOLV TN" by the company Finetex, octyl palmitate, isopropyl lanolate or triglycerides, including those of capric/caprylic acids), or oxyethylenated or oxypropylenated fatty ethers and esters; silicone oils (cyclomethicone, polydimethylsiloxanes or PDMS) or fluorinated oils, or polyalkylenes.

Mention may be made, as waxy compounds, of paraffin, carnauba wax, beeswax or hydrogenated castor oil.

Mention may be made, among organic solvents, of lower alcohols and polyols.

The thickeners can be selected in particular from crosslinked polyacrylic acids or modified or unmodified guar gums and celluloses, such as hydroxypropylated guar gum, methylhydroxyethylcellulose and hydroxypropylmethylcellulose.

Of course, a person skilled in the art will take care to choose the optional additional compound or compounds mentioned above (in particular the additional screening agents) and/or their amounts so that the advantageous properties intrinsically attached to the ternary combination in accordance with the invention are not, or not substantially, detrimentally affected by the envisaged addition or additions and so that the compositions of the invention exhibit good cosmetic properties.

The compositions according to the invention can be prepared according to techniques well known to a person skilled in the art, in particular those intended for the preparation of emulsions of oil-in-water or water-in-oil type.

This composition can in particular be provided in the form of a simple or complex emulsion (O/W, W/O, O/W/O or W/O/W), such as a cream or a milk, or in the form of a gel or of a cream gel, of a powder or of a solid stick and can optionally be packaged as an aerosol and be provided in the form of a foam or of a spray.

The compositions according to the invention are preferably provided in the form of an oil-in-water emulsion.

When it concerns an emulsion, the aqueous phase of the latter can comprise a non-ionic vesicular dispersion prepared according to known processes (Bangham, Stanidish and Watkins, J. Mol. Biol., 13, 238 (1965), FR 2,315,991 and FR 2,416,008, the disclosures of which are specifically incorporated by reference herein).

The cosmetic and/or dermatological composition of the invention can be used as composition for protecting the hair or human epidermis against ultraviolet rays, as anti-sun composition or as make-up product.

When the cosmetic composition according to the invention is used for protecting the human epidermis against UV rays or as anti-sun composition, it can be provided in the form of a suspension or dispersion in solvents or fatty substances, in the form of a non-ionic vesicular dispersion or in the form of an emulsion, preferably of oil-in-water type, such as a cream or a milk, or in the form of an ointment, gel, cream gel, solid stick, aerosol foam or spray.

When the cosmetic composition according to the invention is used for protecting the hair, it can be provided in the form of a hair lacquer, shampoo, lotion, gel, emulsion or non-ionic vesicular dispersion and can constitute, for example, a rinse-out composition, to be applied before or after shampooing, before or after dyeing or bleaching, or before, during or after a permanent-waving or hair-straightening operation, a styling or treating lotion or gel, a lotion or gel for blow-drying or hair setting, or a composition for the permanent-waving, straightening, dyeing or bleaching of the hair.

When the composition is used as a product for making up the eyelashes, eyebrows or skin, such as a cream for treatment of the epidermis, foundation, lip composition, eye shadow, blusher, mascara or eye liner, it can be provided in the anhydrous or aqueous, solid or pasty form, such as oil-in-water or water-in-oil emulsions, non-ionic vesicular dispersions, or suspensions.

By way of indication, for anti-sun formulations in accordance with the invention which exhibit a vehicle of oil-in-water emulsion type, the aqueous phase (comprising in particular the hydrophilic screening agents) generally represents from 50 to 95% by weight, more preferably from 70 to 90% by weight, with respect to the whole formulation, the oily phase (comprising in particular the lipophilic screening agents) preferably from 5 to 50% by weight, more preferably from 10 to 30% by weight, with respect to the whole formulation, and the (co)emulsifier(s) preferably from 0.5 to 20% by weight, more preferably from 2 to 10% by weight, with respect to the whole formulation.

A concrete but in no way limiting example illustrating the invention will now be given.

TESTS:

In the tests described hereinbelow, polyethyleneimine (PEI) with a molecular weight of 700 sold by the company Aldrich has been used.

The percentages of components in the formulae are given by weight with respect to the total weight of the formula.

TEST 1: EX-VIVO Test of inhibition of the photoperoxidation of 4-tert-butyl-4'-methoxydibenzoylmethane by polyethyleneimine under UV-A A thin film of control product (formula A: 4-tert-butyl-4'-methoxydibenzoylmethane) was applied to a first circular filter with an area of 17 $cm^2$ at the rate of approximately 3 $mg/cm^2$. The product containing the polyethyleneimine (product B: 4-tert-butyl-4'-methoxydibenzoylmethane+PEI) was applied to a second filter. The filters were subsequently irradiated under 20 joules UV-A/$cm^2$ using a Biotronic 360 device.

The 4-tert-butyl-4'-methoxydibenzoylmethane peroxides were extracted from the filters using 5 ml of ethanol. The peroxides were assayed in these extracts by HPLC.

The results are expressed as inhibition of the peroxidation of 4-tert-butyl-4'-methoxydibenzoylmethane:

$$\% \text{ inhibition} = \frac{\text{ROOH (formula A)} - \text{ROOH (formula B)}}{\text{ROOH (formula A)}} \times 100$$

ROOH represents the amount of 4tert-butyl-4'-methoxydibenzoylmethane peroxides in the formula (picomoles of peroxides as $H_2O_2$ equivalent per mg of product extracted).

The composition of the formulae A and B is as follows:

| CTFA Name | Formula A | Formula B |
|---|---|---|
| Cetyl alcohol | 5% | 5% |
| Glyceryl stearate | 3% | 3% |
| P.E.G. 50 stearate | 3% | 3% |
| Mineral oil | 20% | 20% |
| Caprylic/capric triglycerides | 3% | 3% |
| 4-tert-Butyl-4'-methoxydibenzoylmethane | 1% | 1% |
| Water | q.s. for 100% | q.s. for 100% |
| Polyethyleneimine | 0% | 0% |

The following results were obtained:

| Formula | Peroxides in pmol/mg |
|---|---|
| Formula A | 2600 |
| Formula B | 1010 | i.e. 60% inhibition of the photoperoxidation of 4-tert-butyl-4'-methoxydibenzoylmethane with respect to the formula A.

TEST 2: Test of photostabilization of 4tert-butyl-4'-methoxydibenzoylmethane by polyethyleneimine under UV-A Films of anti-sun formula were prepared by manually spreading the formula at the rate of 2 mg/cm² over a depolished poly(methyl methacrylate) (PMMA) or depolished glass substrate.

The samples thus prepared were subsequently exposed for 2 H 30 or 4 H 30 to radiation from a Heraeus Sun-test (source: 1.8 kW Arc long Xenon) in a chamber, the temperature of which was adjusted to approximately from 35 to 40° C., in order to simulate natural UV irradiation.

This exposure corresponded to approximately 30 J/cm² UV-A (2 H 30) or 54 J/cm² UV-A (4 H 30).

After exposure, the UV screening agents were extracted with 63 ml of ethanol per sample.

The solutions obtained were analysed by spectrophotometry. The optical density of this solution at the $\lambda_{max}$ of the screening agent was measured.

The screening agents of a sample of control formula (same composition) applied to the depolished PMMA or depolished glass substrate but which has not been subjected to UV irradiation were extracted and analysed in parallel according to the same protocol.

The level of residual screening agents after irradiation is given, for each of the screening agents of the formula, by the ratio of the optical density in the irradiated sample to its optical density in the non-irradiated sample (control sample).

The composition of the formulae tested was as follows:

| | A' | B' |
|---|---|---|
| Polyethylene glycol stearate (40 EO) (sold by ICI under the tradename MYRJ 52) | 4 | 4 |
| Sorbitan tristearate (sold by ICI under the tradename SPAN 65) | 0.9 | 0.9 |
| Cetyl alcohol | 4 | 4 |
| Glyceryl stearate, pharmaceutical grade (Stearinerie Dubois) | 3.3 | 3.3 |
| Benzoate of $C_{12}/C_{15}$ alcohols (sold by Witco under the tradename WITCONOL) | 10 | 10 |
| Liquid petrolatum | 5 | 5 |
| 4-tert-Butyl-4'-methoxydlbenzoylmethane | 2 | 2 |
| Polyethyleneimine | / | 8 |
| Hydrochloric acid | / | q.s. neutralization |
| Glycerol | 6 | 6 |
| EDTA | 0.1 | 0.1 |
| Preservatives | q.s. | q.s. |
| Demineralized water q.s. for | 100 g | 100 g |

Irradiation was carried out with 30 J/cm² and the following results were obtained:

| | Formula A' | Formula B' |
|---|---|---|
| % residual screening agent, measured at 358 nm | 27 ± 2 | 40 ± 3 |

TEST 3: Test of photostabilization of 4-tert-butyl-4'-methoxydibenzoylmethane in the presence of 2,4,6-tris[p-(2'-ethylhexyl-1'-oxycarbonyl)anilino]-1,3,5-triazine by polyethyleneimine under UV-A The same protocol as in Test 2 was applied to the following formulae:

| | A" | B" | C" | D" |
|---|---|---|---|---|
| 80/20 Mixture of cetylstearyl alcohol and of oxyethylenated cetylstearyl alcohol (33 EO) (sold by the company Tensia under the tradename DEHSCONET 390) | 7 | 7 | 7 | 7 |
| Mixture of glyceryl mono- and distearate (sold by the company ISP under the tradename CERASYNTH SD) | 2 | 2 | 2 | 2 |
| Cetyl alcohol | 1.5 | 1.5 | 1.5 | 1.5 |
| Polydimethylsiloxane (sold by the company Dow Corning under the tradename DC200 Fluid) | 1.5 | 1.5 | 1.5 | 1.5 |
| Benzoate of $C_{12}/C_{15}$ alcohols (sold by the company Witco under the tradename WITCONOL TN) | 15 | 15 | 15 | 15 |
| 2,4,6-Tris[p-(2'-ethylhexyl-1'-oxycarbonyl)anilino]-1,3,5-triazine | 1.5 | / | 1.5 | 1.5 |
| 4-tert-Butyl-4'-methoxydibenzoylmethane | / | 0.5 | 0.5 | 0.5 |
| EDTA | / | 0.1 | 0.1 | 0.1 |
| Polyethyleneimine | / | / | / | 4 |
| Hydrochloric acid | / | / | / | q.s. pH 7 |
| Preservatives | q.s. | q.s. | q.s. | q.s. |
| Demineralized water q.s. for | 100 g | 100 g | 100 g | 100 g |

Irradiation was carried out with 54 J/cm². The following results were obtained:

| | % residual screening agent [2,4,6-tris[p-(2'-ethylhexyl-1'-oxycarbonyl)-anilino]-1,3,5-triazine], measured at 312 nm | % residual screening agent [4-tert-butyl-4'-methoxydibenzoyl-methane), measured at 358 nm |
|---|---|---|
| Formula A" | 102 ± 9 | — |
| Formula B" | — | 40 ± 4 |
| Formula C" | 89 ± 3 | 39 ± 5 |
| Formula D" | 97 ± 4 | 60 ± 12 |

We claim:

1. A cosmetic and/or dermatological composition comprising, in a cosmetically and/or dermatologically acceptable vehicle:

a) at least one polyamino polymer selected from:
(A) a polyalkylene polyamine polymers selected from:
(i) polyalkylene polyamines;
(ii) alkylated derivatives of polyalkylene polyamines;
(iii) addition products of alkylcarboxylic acids with polyalkylene polyamines (A)(i);
(iv) addition products of ketones and aldehydes with polyalkylene polyamines (A)(i);
(v) addition products of isocyanates and isothiocyanates with polyalkylene polyamines (A)(i);
(vi) addition products of alkylene oxide and poly (alkylene oxide) block polymers with polyalkylene polyamines (A)(i);
(vii) quaternized derivatives of polyalkylene polyamines (A)(i);
(viii) addition products of a silicone with polyalkylene polyamines (A)(i);
(ix) a copolymer of dicarboxylic acid and polyalkylene polyamines (A)(i);
(B) polyvinylimidazoles;
(C) polyvinylpyridines;
(D) addition products of 1-vinylimidazole monomers of formula (I):

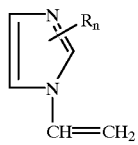

(I)

in which:
R radicals independently represent H or a saturated or unsaturated, linear or cyclic, $C_1$–$C_6$ alkyl radical,
n is an integer ranging from 1 to 3, with polyalkylene polyamines (A)(i) to (A)(ix);
(E) polymers based on amino acids containing a basic side chain; and
(F) crosslinked derivatives of the polymers (A)(i) to (A)(ix), (B), (C), (D) and (E); and b) at least one dibenzoylmethane derivative corresponding to the following formula (V):

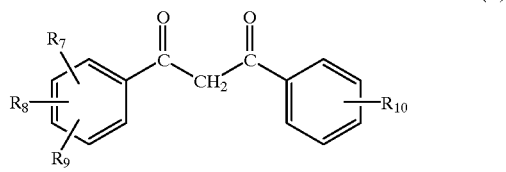

(V)

in which:
$R_7$, $R_8$, $R_9$, and $R_{10}$, independently represent hydrogen or a hydroxyl radical or a linear or branched $C_1$–$C_8$ alkyl radical or a linear or branched $C_1$–$C_8$ alkoxy radical wherein the at least of polyamino polymer improves the photostability of the cosmetic and/or dermatological composition as compared to the photostability of a cosmetic and/or dermatological composition absent at least one polyamino polymer.

2. A cosmetic and/or dermatological composition according to claim 1, wherein said (A)(i) polyalkylene polyamines comprise from 7 to 20,000 repeat units.

3. A cosmetic and/or dermatological composition according to claim 1, wherein said at least one polyamino polymer is selected from polyamino polymers comprising at least 5% tertiary amine functional groups.

4. A cosmetic and/or dermatological composition according to claim 3, wherein said at least one polyamino polymer is selected from polyamino polymers comprising at least 10% tertiary amine functional groups.

5. A cosmetic and/or dermatological composition according to claim 4, wherein said at least one polyamino polymer is selected from polyamino polymers comprising at least 20% tertiary amine functional groups.

6. A cosmetic and/or dermatological composition according to claim 1, wherein said at least one polyamino polymer is selected from:
(A)
(i) hyperbranched polyethyleneimines;
(ii) alkylated polyethyleneimine derivatives;
(iii) addition products of alkylcarboxylic acids with polyethyleneimine;
(iv) addition products of ketones and aldehydes with polyethyleneimine;
(v) addition products of isocyanates and isothiocyanates with polyethyleneimine;
(vi) addition products of alkylene oxide and poly (alkylene oxide) block polymers with polyethyleneimine;
(vii) quaternized derivatives of polyethyleneimine;
(viii) addition products of a silicone with polyethyleneimine;
(ix) a copolymer of dicarboxylic acid and of polyethyleneimine; and
(B) polyvinylimidazoles.

7. A cosmetic and/or dermatological composition according to claim 6, wherein said at least one polyamino polymer is selected from hyperbranched polyethyleneimines.

8. A cosmetic and/or dermatological composition according to claim 1, wherein said at least one polyamino polymer is present in an amount ranging from 0.01% to 50% by weight with respect to the total weight of said cosmetic and/or dermatological composition.

9. A cosmetic and/or dermatological composition according to claim 8, wherein said at least one polyamino polymer is present in an amount ranging from 0.1% to 30% by weight with respect to the total weight of said cosmetic and/or dermatological composition.

10. A cosmetic and/or dermatological composition according to claim 1, wherein said at least one dibenzoylmethane derivative is selected from:

2-methyldibenzoylmethane, 4-methyldibenzoylmethane, 4-isopropyidibenzoylmethane, 4-tert-butyidibenzoylmethane, 2,4-dimethyldibenzoylmethane, 2,5-dimethyldibenzoylmethane, 4,4'-diisopropyidibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and 4,4'-dimethoxydibenzoylmethane.

11. A cosmetic and/or dermatological composition according to claim 10 wherein said at least one dibenzoylmethane derivative is 4-tert-butyl-4'-methoxydibenzoylmethane or 4-isopropyldibenzoylmethane.

12. A cosmetic and/or dermatological composition according to claim 1, wherein said at least one dibenzoylmethane derivative is present in an amount ranging from 0.2% to 15% by weight with respect to the total weight of said cosmetic and/or dermatological composition.

13. A cosmetic and/or dermatological composition according to claim 12, wherein said at least one dibenzoylmethane derivative is present in an amount ranging from 0.2% to 10% by weight with respect to the total weight of said cosmetic and/or dermatological composition.

14. A cosmetic and/or dermatological composition according to claim 1, wherein said cosmetic composition further comprises at least one 1,3,5-triazine derivative corresponding to the following formula (I):

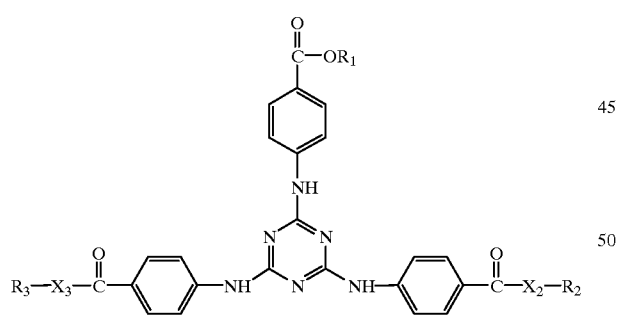

in which:

$X_2$ and $X_3$ independently represent oxygen or the —NH— radical;

$R_1$, $R_2$ and $R_3$ independently are selected from: hydrogen; alkali metasl; ammonium radicals optionally substituted by at least one radical selected from alkyl and hydroxyalkyl radicals; linear and branched $C_1$–$C_{18}$ alkyl radicals; $C_5$–$C_{12}$ cycloalkyl radicals optionally substituted by at least one $C_1$–$C_4$ alkyl radical; polyoxyethylene radicals comprising from 1 to 6 ethylene oxide units, wherein the terminal OH group is methylated; and radicals of formulae (II), (III) or (IV):

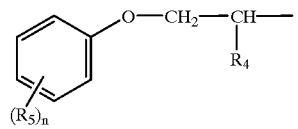

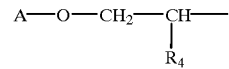

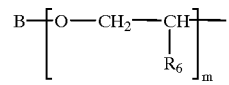

in which:

$R_4$ is hydrogen or a methyl radical;

$R_5$ is a $C_1$–$C_9$ alkyl radical;

n is an integer ranging from 0 to 3;

m is an integer ranging from 1 to 10;

A is a $C_4$–$C_8$ alkyl radical or a $C_5$–$C_8$ cycloalkyl radical;

B is selected from: linear and branched $C_1$–$C_8$ alkyl radicals; $C_5$–$C_8$ cycloalkyl radicals; and aryl radicals optionally substituted by at least one $C_1$–$C_4$ alkyl radical;

$R_6$ is hydrogen or a methyl radical, wherein in formula (I), when $X_2$ or $X_3$ represent a —NH— radical, $R_2$ and $R_3$ are not an alkali metal or an ammonium radical.

15. A cosmetic and/or dermatological composition according to claim 14, wherein said at least one 1,3,5-triazine derivative is selected from derivatives of formula (I) exhibiting all the following characteristics:

$X_2$ and $X_3$ are identical and represent oxygen;

$R_1$ is selected from: $C_5$–$C_{12}$ cycloalkyl radicals optionally substituted by one or more $C_1$–$C_4$ alkyl radicals; and radicals of formulae (II), (III) and (IV) in which:

B is a $C_1$–$C_4$ alkyl radical;

$R_6$ is the methyl radical;

$R_2$ and $R_3$ independently are selected from: hydrogen; alkali metals; ammonium radicals optionally substituted by at least one radical selected from alkyl and hydroxyalkyl radicals; linear and branched $C_1$–$C_{18}$ alkyl radicals; $C_5$–$C_{12}$ cycloalkyl radicals optionally substituted by at least one $C_1$–$C_4$ alkyl radical; and radicals of formulae (II), (III) and (IV) in which:

B is a $C_1$–$C_4$ alkyl radical; and $R_6$ is the methyl radical.

16. A cosmetic and/or dermatological composition according to claim 14, wherein said at least one 1,3,5-triazine derivative is selected from derivatives of formula (I) exhibiting all the following characteristics:

$X_3$ represents the —NH— radical;

$R_3$ is selected from: linear and branched $C_1$–$C_{18}$alkyl radicals; and $C_5$–$C_{12}$cycloalkyl radicals optionally substituted by at least one $C_1$–$C_4$ alkyl radical;

$R_1$ is selected from: hydrogen; alkali metals; ammonium radicals; radicals of formula (IV); linear and branched $C_1$–$C_{18}$ alkyl radicals; $C_5$–$C_{12}$ cycloalkyl radicals optionally substituted by at least one $C_1$–$C_4$ alkyl radical;

if $X_2$ is a —NH— radical, $R_2$ is selected from: linear and branched $C_1$–$C_{18}$ alkyl radicals; and $C_5$–$C_{12}$ cycloalkyl radicals optionally substituted by at least one $C_1$–$C_4$ alkyl radical.

if $X_2$ is oxygen, $R_2$ is selected from hydrogen; alkali metals; ammonium radicals; radicals of formula (IV); linear and branched $C_1$–$C_{18}$ alkyl radicals; and $C_5$–$C_{12}$ cycloalkyl radicals optionally substituted by at least one $C_1$–$C_4$ alkyl radical.

17. A cosmetic and/or dermatological composition according to claim 14, wherein said at least one 1,3,5-triazine derivative is selected from derivatives of formula (I) exhibiting all the following characteristics:

$X_2$ is oxygen;

$X_3$ is the —NH— radical;

$R_3$ is selected from: linear and branched $C_1$–$C_{18}$ alkyl radicals; $C_5$–$C_{12}$ cycloalkyl radicals optionally substituted by one or more $C_1$–$C_4$ alkyl radicals;

$R_1$ is selected from: hydrogen; alkali metals; ammonium radicals; radicals of formula (IV); linear and branched $C_1$–$C_{18}$ alkyl radicals; $C_5$–$C_{12}$ cycloalkyl radicals optionally substituted by one or more $C_1$–$C_4$ alkyl radicals; and $R_2$ is selected from hydrogen; alkali metals; ammonium radicals; radicals of formula (IV); linear and branched $C_1$–$C_{18}$ alkyl radicals; $C_5$–$C_{12}$ cycloalkyl radical optionally substituted by at least one $C_1$–$C_4$ alkyl radicals.

18. A cosmetic and/or dermatological composition according to claim 16, wherein said at least one 1,3,5-triazine derivative corresponds to the formula:

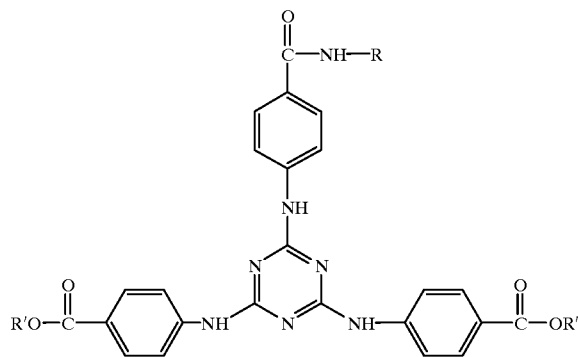

in which:

R' denotes a 2-ethylhexyl radical and R denotes a tert-butyl radical.

19. A cosmetic and/or dermatological composition according to claim 14, wherein said at least one 1,3,5-triazine derivative is selected from derivatives of formula (I) exhibiting all the following characteristics:

$X_2$ and $X_3$ are identical and represent oxygen; and $R_1$, $R_2$, and $R_3$ are identical and represent a $C_6$–$C_{12}$ alkyl radical or a polyoxyethylene radical comprising from 1 to 6 ethylene oxide units, wherein the terminal OH group is methylated.

20. A cosmetic and/or dermatological composition according to claim 19, wherein said at least one 1,3,5-triazine derivative corresponds to the formula:

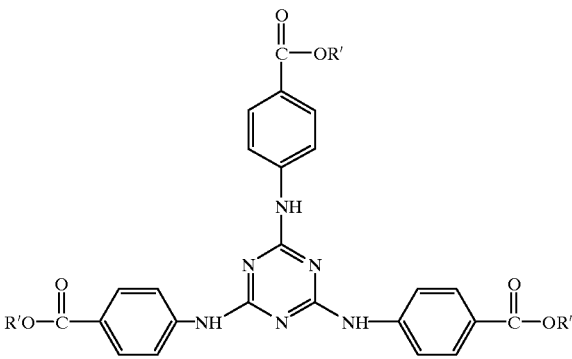

in which R' denotes a 2-ethylhexyl radical.

21. A cosmetic and/or dermatological composition according to claim 14, wherein said at least one 1,3,5-triazine derivative is present in an amount ranging from 0.5% to 20% by weight with respect to the total weight of said cosmetic composition.

22. A cosmetic and/or dermatological composition according to claim 21, wherein said at least one any 1,3,5-triazine derivative is present in an amount ranging from 1% to 10% by weight with respect to the total weight of said cosmetic composition.

23. A cosmetic and/or dermatological composition according to claim 1, wherein said at least one polyamino polymer is introduced in a neutralized form.

24. A cosmetic and/or dermatological composition according to claim 1, wherein said cosmetic composition further comprises at least one metal oxide nanopigment.

25. A cosmetic and/or dermatological composition according to claim 24, wherein said at least one metal oxide nanopigment is selected from titanium oxides, zinc oxides, cerium oxides, and zirconium oxides.

26. A cosmetic and/or dermatological composition according to claim 25, wherein said at least one metal oxide nanopigment is a titanium oxide nanopigment.

27. A cosmetic and/or dermatological composition according to claim 24, wherein said at least one metal oxide nanopigment is present in an amount ranging from 0.1 and 20% by weight with respect to the total weight of said cosmetic composition.

28. A cosmetic and/or dermatological composition according to claim 27, wherein said at least one metal oxide nanopigment is present in an amount ranging from 0.25 and 15% by weight with respect to the total weight of said cosmetic composition.

29. A cosmetic and/or dermatological composition according to claim 1, wherein said cosmetic and/or dermatological composition further comprises at least one additional sunscreen agent.

30. A cosmetic and/or dermatological composition according to claim 1, wherein said cosmetic and/or dermatological composition further comprises at least one artificial tanning agent or self-tanning agent.

31. A cosmetic and/or dermatological composition according to claim 1, wherein said cosmetic and/or dermatological composition further comprises at least one pigment other than a metal oxide nanopigment.

32. A cosmetic and/or dermatological composition according to claim 1, wherein said cosmetic and/or dermatological composition further comprises at least one conventional cosmetic adjuvant.

33. A cosmetic and/or dermatological composition according to claim 1, wherein said cosmetic and/or dermatological composition is in the form of a simple or complex emulsion, a gel, a cream gel, a powder, a solid, a foam or a spray.

34. A cosmetic and/or dermatological composition according to claim 1, wherein said cosmetic and/or dermatological composition is in the form of an oil-in-water emulsion.

35. A cosmetic and/or dermatological composition according to claim 1, wherein said at least one polyamino polymer is an antioxidizing agent with respect to said at least one dibenzoylmethane derivative.

36. A cosmetic and/or dermatological composition according to claim 1, wherein said at least one polyamino polymer improves the stability to UV radiation of said at least one dibenzoylmethane derivative as compared the stability to UV radiation of said at least one dibenzoylmethane derivative without at least one polyamino polymer.

37. A process for improving the stability to UV radiation of cosmetic and/or dermatological compositions comprising adding to said cosmetic and/or dermatological compositions at least one dibenzoylmethane derivative to stabilize said compositions to UV radiation, wherein said dibenzoylmethane derivative corresponds to the following formula (V):

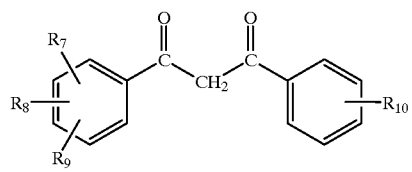

in which:

$R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical, comprising including in said cosmetic and/or dermatological composition an effective amount of at least one polyamino polymer selected from:

(A) a polyalkylene polyamine or a polyalkylene polyamine derivative selected from:
(i) polyalkylene polyamines;
(ii) alkylated derivatives of polyalkylene polyamines;
(iii) addition products of alkylcarboxylic acids with polyalkylene polyamines (A)(i);
(iv) addition products of ketones and aldehydes with polyalkylene polyamines(A)(i);
(v) addition products of isocyanates and isothiocyanates with polyalkylene polyamines(A)(i);
(vi) addition products of alkylene oxide and poly(alkylene oxide) block polymers with polyalkylene polyamines (A)(i);
(vii) quaternized derivatives of polyalkylene polyamines (A)(i);
(viii) addition products of a silicone with polyalkylene polyamines (A)(i);
(ix) a copolymer of dicarboxylic acid and of polyalkylene polyamines (A)(i);
(B) polyvinylimidazoles;
©) polyvinylpyridines;
(D) addition products of 1-vinylimidazole monomers of formula (I):

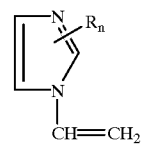

in which:

R radicals independently represent H or a saturated or unsaturated, linear or cyclic, $C_1$–$C_6$ alkyl radical, n is an integer ranging from 1 to 3, with polyalkylene polyamines (A)(i) to (A)(ix);

(E) polymers based on amino acids containing a basic side chain; and (F) crosslinked derivatives of the polymers (A)(i) to (A)(ix), (B), (C), (D) and (E).

38. A cosmetic and/or dermatological composition according to claim 14, wherein said at least one polyamino polymer improves the stability to UV radiation of said at least one 1,3,5-triazine derivative as compared the stability to UV radiation of said at least one 1,3,5-triazine derivative without at least one polyamino polymer.

39. A process for improving the stability to UV radiation of cosmetic and/or dermatological compositions comprising adding to said cosmetic and/or dermatological compositions at least one dibenzoylmethane derivative to stabilize said compositions to UV radiation, wherein said dibenzoylmethane derivative corresponds to the following formula (V):

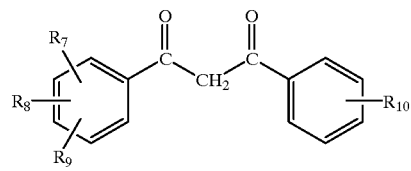

in which:

$R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical, and at least one 1,3,5-triazine derivative corresponding to the following formula (I):

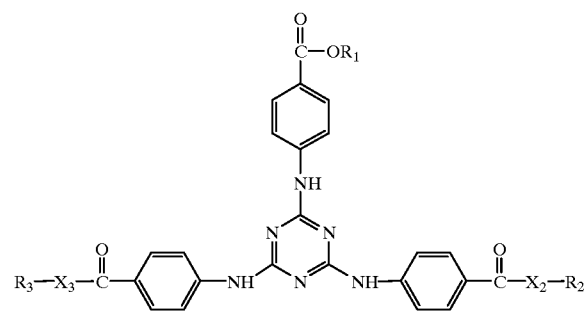

in which:

$X_2$ and $X_3$ independently represent oxygen or the —NH— radical;

$R_1$, $R_2$ and $R_3$ independently are selected from: hydrogen; alkali metals; ammonium radicals optionally substituted by at least one alkyl or hydroxyalkyl radicals; linear and branched $C_1$–$C_{18}$ alkyl radicals; $C_5$–$C_{12}$ cycloalkyl radicals optionally substituted by at least one $C_1$–$C_4$ alkyl radical; polyoxyethylene radicals comprising from 1 to 6 ethylene oxide units, wherein the terminal OH group is methylated; and radicals of formulae (II), (III) and (IV):

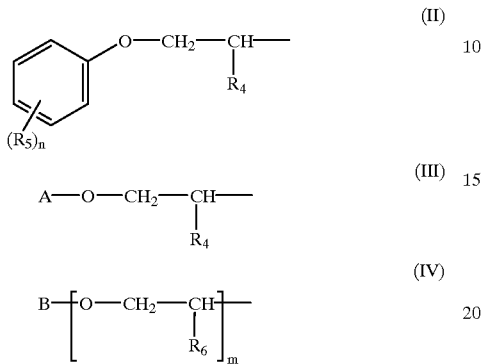

in which:
$R_4$ is hydrogen or a methyl radical;
$R_5$ is a $C_1$–$C_9$ alkyl radical;
n is an integer ranging from 0 to 3;
m is an integer ranging from 1 to 10;
A is a $C_4$–$C_8$ alkyl radical or a $C_5$–$C_8$ cycloalkyl radical;
B is selected from: a linear or branched $C_1$–$C_8$ alkyl radical; a $C_5$–$C_8$ cycloalklyl radical; and an aryl radical optionally substituted by at least one $C_1$–$C_4$ alkyl radical;
$R_6$ is hydrogen or a methyl radical, wherein in formula (I), when $X_2$ or $X_3$ represent a —NH— radical, $R_2$ and $R_3$ are not an alkali metal or an ammonium radical, comprising including in said cosmetic and/or dermatological composition an effective amount of at least one polyamino polymer selected from:
(A) a polyalkylene polyamine or a polyalkylene polyamine derivative selected from:
 (i) polyalkylene polyamines;
 (ii) alkylated derivatives of polyalkylene polyamines;
 (iii) addition products of alkylcarboxylic acids with polyalkylene polyamines (A)(i);
 (iv) addition products of ketones and aldehydes with polyalkylene polyamines(A)(i);
 (v) addition products of isocyanates and isothiocyanates with polyalkylene polyamines(A)(i);
 (vi) addition products of alkylene oxide or of poly(alkylene oxide) block polymers with polyalkylene polyamines (A)(i);
 (vii) quaternized derivatives of polyalkylene polyamines (A)(i);
 (viii) addition products of a silicone with polyalkylene polyamines (A)(i);
 (ix) a copolymer of dicarboxylic acid and of polyalkylene polyamines (A)(i);
(B) polyvinylimidazoles;
(C) polyvinylpyridines;
(D) addition products of 1-vinylimidazole monomers of formula (I):

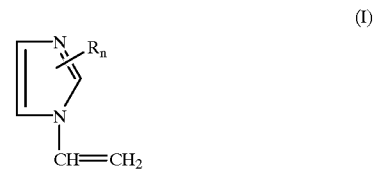

in which:
R radius independently represent H or a saturated or unsaturated, linear or cyclic, $C_1$–$C_6$ alkyl radical,
n is an integer ranging from 1 to 3, with polyalkylene polyamines (A)(i) to (A)(ix);
(E) polymers based on amino acids containing a basic side chain; and
(F) crosslinked derivatives of the polymers (A)(i) to (A)(ix), (B), (C), (D) and (E).

* * * * *

UNITED STATES PATENT AND TRADEMARK OFFICE
CERTIFICATE OF CORRECTION

PATENT NO.    : 6,328,981 B1                                        Page 1 of 1
DATED         : February 4, 2002
INVENTOR(S)   : Boudiaf Boussouira et al.

It is certified that error appears in the above-identified patent and that said Letters Patent is hereby corrected as shown below:

Title page,
Item [57], line 1, "dermatalogoical" should read -- dermatological --.

Column 22,
Line 15, after "least", delete "of" and insert -- one -- therefor.

Column 23,
Line 7, "isopropyidizenzoylmethane" should read -- isopropyldizenzoylmethane --.
Line 8, "butyidibenzoylmethane" should read -- butyldibenzoylmethane --.
Line 11, "diisopropyidibenzoylmethane" should read -- diisopropyldibenzoylmethane --.

Signed and Sealed this

Twenty-first Day of May, 2002

Attest:

Attesting Officer

JAMES E. ROGAN
Director of the United States Patent and Trademark Office